United States Patent [19]

Inui et al.

[11] Patent Number: 6,075,159

[45] Date of Patent: Jun. 13, 2000

[54] PHOSPHITE, A PROCESS FOR PRODUCING THE SAME AND A USE THEREOF

[75] Inventors: Naoki Inui, Nara; Taketoshi Kikuchi; Kanako Fukuda, both of Osaka; Takashi Sanada, Chiba, all of Japan

[73] Assignee: Sumitomo Chemical Company, Limited, Osaka, Japan

[21] Appl. No.: 08/961,183

[22] Filed: Oct. 30, 1997

[30] Foreign Application Priority Data

Nov. 1, 1996 [JP] Japan .................................. 8-291981
Jun. 24, 1997 [JP] Japan .................................. 9-167134

[51] Int. Cl.$^7$ ........................................................ C07F 9/06
[52] U.S. Cl. ............................... 558/170; 558/73; 558/83; 558/92; 558/95
[58] Field of Search .............................. 558/73, 83, 92, 558/95, 170

[56] References Cited

FOREIGN PATENT DOCUMENTS 0 168 721-A1  1/1986  European Pat. Off. .
0 617 041-A2  9/1994  European Pat. Off. .
5-86084       4/1994  Japan .

OTHER PUBLICATIONS

CA:100:103496 abs of Huaxue Shiji by Lu 5(6) pp. 359–60, 1983.

CA:78:30865 abs of JP47031927, Aug. 1972.

CA:118:81025 abs of Phosphorus sulfur silicaon and related elements by Page 70(3–4) pp. 205–10, 1992.

*Primary Examiner*—Gary Geist
*Assistant Examiner*—Jean F. Vollano
*Attorney, Agent, or Firm*—Pillsbury Madison & Sutro LLP

[57] ABSTRACT

A phosphite represented by the formula (I):

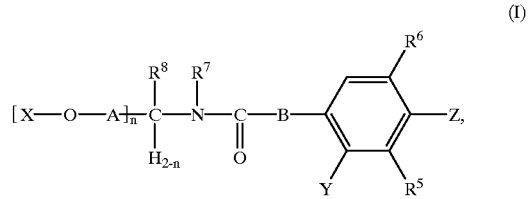

wherein n repesents 1 or 2; A represents alkylene; B represents a direct bond or alkylene; one of Y and Z represents a hydroxyl group, alkoxy or aralkyloxy, and the other one represents a hydrogen atom or alkyl; X represents a group of formula (II):

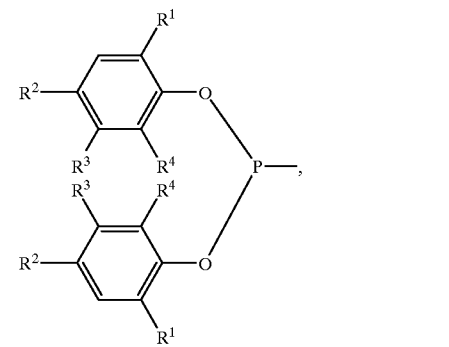

wherein $R^1$ and $R^2$ represent a hydrogen atom, an alkyl group, a cycloalkyl group, an alkylcycloalkyl group, an aralkyl group or a phenyl group; $R^3$ represents a hydrogen atom or an alkyl group; and $R^4$ represents a hydrogen atom, an alkyl group, a cycloalkyl group, an alkylcycloalkyl group, an aralkyl group or a phenyl group, or $R^4$ may be combined to form a direct bond, a sulfur bond (—S—), or an unsubstituted or substituted methylene group; $R^5$ and $R^6$ independently represent a hydrogen atom, an alkyl group, a cycloalkyl group, an alkylcycloalkyl group, an aralkyl group or a phenyl group;

$R^8$ represents a hydrogen atom or an alkyl group; and $R^7$ represents a hydrogen atom or an alkyl group or —CH(R8)—A—O—X; and the organic phosphorus compound is useful as a stabilizer for an organic material.

9 Claims, No Drawings

PHOSPHITE, A PROCESS FOR PRODUCING THE SAME AND A USE THEREOF

The present invention relates to a novel phosphite, and a process for producing the same and its use as a stabilizer for an organic material.

It has been known that organic materials such as thermoplastic resins, thermosetting resins, natural or synthetic rubbers, mineral oils, lubricating oils, adhesives and paints are deteriorated on their production, processing and use by an action of heat, oxygen, etc. As a result, their commercial value is drastically damaged with deterioration of physical strength, change in flow properties, coloring, deterioration of surface properties, etc., which are caused by chain scission and crosslinking. It has hitherto been known that the organic materials are stabilized by containing various phenolic antioxidants and phosphorous antioxidants for preventing heat deterioration and oxidation deterioration.

As the phosphorous antioxidant, for example, tris(2,4-di-t-butylphenyl)phosphite is used. However, these known phosphorous antioxidants do not give sufficient stabilization effect to heat deterioration and oxidation deterioration.

For solving the problem of the known phosphorous antioxidant, a cyclic phosphite having a carbonyloxyalkylene group, such as 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine is suggested (JP-A-5-86084). Although the stabilizing effect of the cyclic phosphite to heat deterioration and oxidation deterioration is improved, they are still not satisfactory. Therefore, development of the more improved antioxidant has been desired.

The present inventors have intensively studied about the phosphorous compound. As a result, it has been found that specific phosphites having a carbonylamidealkylene group in place of a carbonyloxyalkylene group exhibit excellent stabilizing effect. Thus, the present invention has been accomplished.

The present invention provides a phosphite represented by the formula (I):

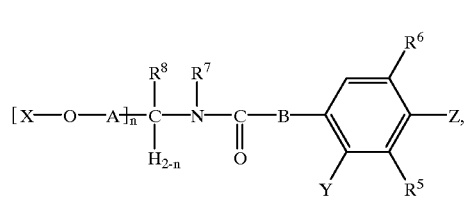

(I)

wherein n represents 1 or 2;

A represents an alkylene group having 1 to 8 carbon atoms;

B represents a direct bond or an alkylene group having 1 to 8 carbon atoms;

one of Y and Z represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms;

X represents a phosphorous-containing group represented by the formula (II):

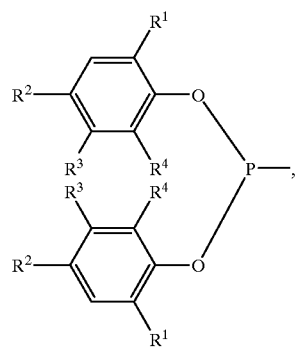

(II)

wherein $R^1$ and $R^2$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents a hydrogen atom or an alkyl group having 1 to 8 carbon atoms; and $R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond (—S—), or a methylene group which is optionally substituted with alkyl having 1 to 8 carbon atoms or cycloalkyl having 5 to 8 carbon atoms;

$R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group;

$R^8$ represents a hydrogen atom or an alkyl group having 1 to 8 carbon atoms; and $R^7$ represents a hydrogen atom or an alkyl group having 1 to 8 carbon atoms when n is 2, or $R^7$ represents a hydrogen atom, an alkyl group having 1 to 8 carbon atoms or a group of —CH($R^8$)—A—O—X (in which $R^8$, A and X are as defined above) when n is 1.

The present invention also provides a process for producing the phosphite represented by the formula (I).

The present invention further provides use of the phosphite represented by the formula (I) as a stabilizer for an organic material.

The substituents $R^1$, $R^2$, $R^5$ and $R^6$ in the formula (I) independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, preferably an alkyl group having 1 to 8 carbon atoms, a cycloalkyl group having 5 to 8 carbon atoms or an alkylcycloalkyl group having 6 to 12 carbon atoms.

Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Examples of the cycloalkyl group having 5 to 8 carbon atoms include cyclopentyl, cyclohexyl, cycloheptyl and cyclooctyl.

Examples of the alkylcycloalkyl group having 6 to 12 carbon atoms include 1-methylcyclopentyl, 1-methylcyclohexyl and 1-methyl-4-i-propylcyclohexy.

Examples of the aralkyl group having 7 to 12 carbon atoms include benzyl, α-methylbenzyl and α,α-dimethylbenzyl.

More preferably, $R^1$ is a t-alkyl group such as t-butyl, t-pentyl and t-octyl. $R^2$ is more preferably an alkyl group having 1 to 5 carbon atoms, such as methyl, ethyl, n-propyl, i-propyl, n-butyl, i-butyl, sec-butyl, t-butyl and t-pentyl. Particularly methyl, t-butyl or t-pentyl is preferable as $R^2$.

$R^5$ is more preferably methyl, t-butyl, t-pentyl or t-octyl. $R^6$ is more preferably a hydrogen atom, methyl, t-butyl, t-pentyl or t-octyl.

the substituent $R^3$ represents a hydrogen atom or an alkyl group having 1 to 8 carbon atoms. Examples of the alkyl group having 1 to 8 carbon atoms as $R^3$ include methyl, ethyl, n-propyl, i-propyl, n-butyl, i-butyl, sec-butyl, t-butyl, t-pentyl, i-octyl, t-octyl and 2-ethylhexyl. $R^3$ is preferably a hydrogen atom or an alkyl group having 1 to 5 carbon atoms, particularly a hydrogen atom or a methyl group.

$R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond (—S—), or a methylene group which is optionally substituted with alkyl having 1 to 8 carbon atoms or cycloalkyl having 5 to 8 carbon atoms.

Examples of the alkyl group having 1 to 8 carbon atoms as $R^4$ include methyl, ethyl, n-propyl, i-propyl, n-butyl, i-butyl, sec-butyl, t-butyl, t-pentyl, i-octyl, t-octyl and 2-ethylhexyl.

Examples of the cycloalkyl group having 5 to 8 carbon atoms as $R^4$ include cyclopentyl, cyclohexyl, cycloheptyl and cyclooctyl.

Examples of the alkylcycloalkyl group having 6 to 12 carbon atoms as $R^4$ include 1-methylcyclopentyl, 1-methylcyclohexyl and 1-methyl-4-i-propylcyclohexyl.

Examples of the aralkyl group having 7 to 12 carbon atoms as $R^4$ include benzyl, α-methylbenzyl, α,α-dimethylbenzyl.

It is preferable that $R^4$ is a hydrogen atom, methyl or a t-alkyl group such as t-butyl, t-pentyl and t-octyl, or that $R^4$ are combined with each other to form a direct bond, a sulfur bond (—S—), an unsubstituted methylene group and a methylene group substituted with methyl, ethyl, n-propyl, i-propyl, n-butyl, i-butyl and t-butyl.

The linking group "A" in the formula (I) represents an alkylene group having 1 to 8 carbon atoms, and "B" in the formula (I) represents a direct bond or an alkylene group having 1 to 8 carbon atoms. Examples of the alkylene group as A or B include methylene, ethylene, propylene, butylene, pentamethylene, hexamethylene, octamethylene, 1,1-dimethylethylene and 2,2-dimethyl-1,3-propylene. Preferably, it is methylene, ethylene or propylene.

The substituent $R^8$ represents a hydrogen atom or an alkyl group having 1 to 8 carbon atoms. $R^7$ represents a hydrogen atom or an alkyl group having 1 to 8 carbon atoms when n is 2, or represents a hydrogen atom, an alkyl group having 1 to 8 carbon atoms or a group of —CH($R^8$)—A—O—X (in which $R^8$, A and X are as defined above) when n is 1. Examples of the alkyl group having 1 to 8 carbon atoms as $R^7$ or $R^8$ include methyl, ethyl, n-propyl, i-propyl, n-butyl, i-butyl, sec-butyl, t-butyl, t-pentyl, i-octyl, t-octyl and 2-ethylhexyl.

$R^8$ is preferably a hydrogen atom, methyl, ethyl, t-butyl and the like, and $R^7$ is preferably a hydrogen atom, methyl, ethyl, t-butyl, a group of —CH($R^8$)—A—O—X and the like.

One of Y and Z in the formula (I) represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms.

Examples of the alkyl group having 1 to 8 carbon atoms as Y or Z include methyl, ethyl, n-propyl, i-propyl, n-butyl, i-butyl, sec-butyl, t-butyl, t-pentyl, i-octyl, t-octyl and 2-ethylhexyl.

Examples of the alkoxy group having 1 to 8 carbon atoms include an alkoxy group whose alkyl moiety is methyl, ethyl, n-propyl, i-propyl, n-butyl, i-butyl, sec-butyl, t-butyl, t-pentyl, i-octyl, t-octyl or 2-ethylhexyl.

Examples of the aralkyloxy group having 7 to 12 carbon atoms include an aralkyloxy group whose aralkyl moiety is benzyl, α-methylbenzyl or α,α-dimethylbenzyl.

One of Y and Z is preferably a hydroxyl group or a methoxy group.

The phosphites represented by the above formula (I) can be produced, for example, by reacting phenols or bisphenols represented by the following formula (III):

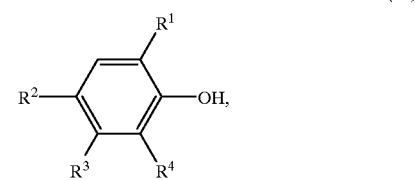

wherein $R^1$, $R^2$, $R^3$ and $R^4$ are as defined above, phosphorous trihalide and an alcohol represented by the formula (IV):

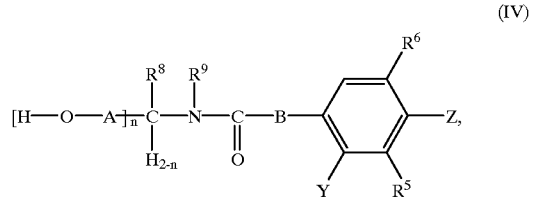

wherein n, A, B, Y, Z, $R^5$, $R^6$ and $R^8$ are as defined above; and $R^9$ represents a hydrogen atom or an alkyl group having 1 to 8 carbon atoms when n is 2, or $R^9$ represents a hydrogen atom, an alkyl group having 1 to 8 carbon atoms or a group of —CH($R^8$)—A—O—H (in which $R^8$ and A are as defined above) when n is 1.

Examples of the phosphorous trihalide used in this reaction include phosphorous trichloride and phosphorous tribromide. Among them, phosphorous trichloride is preferably used.

The reaction for producing the phosphite of formula (I) can be accelerated by the coexistence of a dehydrohalogenating agent such as amines, pyridines, pyrrolidines and amides or a hydroxide of an alkaline metal or an alkaline earth metal.

A primary amine, a secondary amine or a tertiary amine may be used as the amine. Examples the amines include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferable.

Examples of the pyridines include pyridine and picoline. Among them, pyridine is preferable. Examples of the pyrrolidines include 1-methyl-2-pyrrolidine.

Examples of the amides include N,N-dimethylformamide and N,N-dimethylacetamide. Among them, N,N-dimethylformamide is preferably used.

Examples of the hydroxide of the alkaline metal or alkaline earth metal include sodium hydroxide and calcium hydroxide. Among them, sodium hydroxide is preferable.

The reaction for producing the phosphite of formula (I) is normally conducted in an organic solvent. The organic solvent is not specifically limited unless the reaction is inhibited. Examples of the organic solvent include aromatic hydrocarbon, aliphatic hydrocarbon, oxygen-containing hydrocarbon and hydrogenated hydrocarbon.

Examples of the aromatic hydrocarbon include benzene, toluene, xylene and ethylbenzene. Examples of the aliphatic hydrocarbon include n-hexane, n-heptane and n-octane. Examples of the oxygen-containing hydrocarbon include diethyl ether, dibutyl ether, tetrahydrofuran and 1,4-dioxane. Examples of the halogenated hydrocarbon include chloroform, carbon tetrachloride, monochlorobenzene, dichloromethane, 1,2-dichloroethane and dichlorobenzene.

Among them, toluene, xylene, n-hexane, n-heptane, diethyl ether, tetrahydrofuran, 1,4-dioxane, chloroform, dichloromethane and the like are preferably used.

The reaction for producing the phosphite of formula (I) may be conducted according to a so-called two-stage reaction method in which a phenol or bisphenol represented by the formula (III) is reacted with the phosphorous trihalide to form an intermediate firstly, and then the intermediate is reacted with the alcohol represented by the formula (IV).

When a phenol is used as the starting compound in the two-stage reaction method, the phosphorous trihalide is preferably used in an amount of about 0.5 to 0.55 mols, more preferably about 0.5 to 0.52 mols, per mol of the phenol. When a bisphenol is used as the starting compound, the phosphorous trihalide is preferably used in an amount of about 1 to 1.1 mols, more preferably about 1 to 1.05 mols, per mol of the bisphenol. When a dehydrohalogenating agent is used in the reaction between a phenol or a bisphenol represented by the formula (III) with a phosphorous trihalide, it is preferably used in an amount of about 0.05 to 2.4 mols, more preferably about 2 to 2.1 mols, per mol of the phosphorous trihalide.

The reaction between a phenol or a bisphenol represented by the formula (III) with a phosphorous trihalide is normally carried out at about 0 to 200° C. It is considered that an intermediate halogenophosphite is produced by this reaction. The resulting reaction mixture is normally fed to the reaction with the alcohol (IV) as it is, although the intermediate in the reaction mixture may be fed to the following reaction after isolation.

The alcohol (IV) is normally used in an amount of about 0.9 to 1.1 mols per mol of the phosphorous trihalide, when n is 1 and $R^9$ hydrogen atom or alkyl having 1–8 carbon atoms.

The alcohol (IV) is normally used in an amount of about 0.45 to 0.55 mols per mol of the phosphorous trihalide, when n is 2 or when n is 1 and $R^9$ is a group of —CH($R^8$)—A—O—H.

In this reaction with the alcohol (IV), the dehydrohalogenating agent can also be used. When the dehydrohalogenating agent is used in the reaction with the alcohol (IV), the amount of the dehydrohalogenating agent is preferably about 0.04 to 1.3 mols per mol of the phosphorous trihalide. When using the excess dehydrohalogenating agent in the first reaction, the amount of the dehydrohalogenating agent in the reaction with the alcohol (IV) is normally calculated by including amount of the residual dehydrohalogenating agent.

The reaction with the alcohol (IV) is normally carried out at the temperature of about 0 to 200° C.

After completion of the reaction, when using the dehydrohalogenating agent, the phosphite (I) of the present invention can be obtained by removing a halogenhalogenate of the dehydrohalogenating agent produced by the reaction, and then removing the solvent, followed by suitable post treatment such as crystallization or column chromatography.

Examples of the phenols represented by the formula (III) as a starting material of the phosphites (I) include 2-methylphenol, 4-methylphenol, 2,4-dimethylphenol, 2,6-dimethylphenol, 2,4,6-trimethylphenol, 2-ethylphenol, 4-ethylphenol, 2,4-diethylphenol, 2,6-diethylphenol, 2,4,6-triethylphenol, 2-t-butylphenol, 4-t-butylphenol, 2-t-butyl-4-methylphenol, 2-t-butyl-5-methylphenol, 2-t-butyl-4-ethylphenol, 2,4-di-t-butylphenol, 2-t-butyl-6-methylphenol, 2-t-butyl-6-ethylphenol, 2,6-di-t-butylphenol, 2,4-dimethyl-6-t-buthylphenol, 2,6-dimethyl-4-t-butylphenyl, 2-methyl-4,6-di-t-butylphenol, 3-methyl-4,6-di-t-butylphenol, 2-ethyl-4,6-di-t-butylphenol, 3-ethyl-4,6-di-t-butylphenol, 4methyl-2,6-di-t-butylphenol, 4-ethyl-2,6di-b-butylphenol, 2,4,6-tri-t-butylphenol, 2,4-di-t-pentylphenol, 2-t-octylphenol, 2,4di-t-octylphenol, 2,6-di-t-octylphenol, 2,4,6-tri-t-octylphenol, 2-nonylphenol, 4-nonylphenol, 2-cyclohexyl-4-methylphenol and 2-(1)-methylcyclohexyl)-4-methylphenol.

Examples of the bisphenol represented by the formula (III) include 2,2'-methylenebis(4-methyl-6-t-butylphenol), 2,2'-methylenebis(4-ethyl-6-t-butylphenol), 2,2'-methylenebis(4-n-propyl-6-t-butylphenol), 2,2'-methylenebis(4-i-propyl-6-t-butylphenol), 2,2'-methylenebis(4-n-butyl-6-t-butylphenol), 2,2'-methylenebis(4-i-butyl-6-t-butylphenol), 2,2'-methylenebis(4,6-di-t-butylphenol), 2,2'-methylenebis(4-t-pentyl-6-t-butylphenol), 2,2'-methylenebis(4-nonyl-6-t-butylphenol), 2,2'-methylenebis(4-t-octyl-6-t-butylphenol), 2,2'-methylenebis(4-methyl-6-t-pentylphenol), 2,2'-methylenebis(4-methyl-6-cyclohexylphenol), 2,2'-methylenebis[4-methyl-6-(α-methylcyclohexyl)phenol)], 2,2'-methylenebis(4-methyl-6-t-nonylphenol), 2,2'-methylenebis(4-methyl-6-t-octylphenol), 2,2'-methylenebis(4,6-di-t-pentylphenol), 2,2'-methylenebis[4-nonyl-6-(αmethylbenzyl)phenol], 2,2'-methylenebis[4-nonyl-6-(α,α-dimethylbenzyl)phenol], 2,2'-ethylidenebis(4-methyl-6-butylphenol), 2,2'-ethylidenebis(4-ethyl-6-t-butylphenol), 2,2'-ethylidenebis(4-n-propyl-6-t-butylphenol), 2,2'-ethylidenebis(4-i-propyl-6-t-butylphenol), 2,2'-ethylidenebis(4-n-butyl-6-t-butylphenol), 2,2'-ethylidenebis(4-i-butyl-6-t-butylphenol), 2,2'-ethylidenebis(4,6-di-t-butylphenol), 2,2'-ethylidenebis(4-t-pentyl-6-butylphenol), 2,2'-ethylidenebis(4-nonyl-6-t-butylphenol), 2,2'-ethylidenebis(4-t-octyl-6-t-butylphenol), 2,2'-ethylidenebis(4-methyl-6-t-pentylphenol), 2,2'-ethylidenebis(4-methyl-6-cyclohexylphenol), 2,2'-ethylidenebis[4-methyl-6-(α-methylcyclohexyl)phenol)], 2,2'-ethylidenebis(4-methyl-6-nonylphenol), 2,2'-ethylidenebis(4-methyl-6-t-octylphenol), 2,2'-ethylidenebis(4,6-di-t-pentylphenol), 2,2'-ethylidenebis[4-nonyl-6-(α-methylbenzyl)phenol], 2,2'-ethylidenebis[4-nonyl-6-(α,α-dimethylbenzyl)phenol], 2,2'-propylidenebis(4-methyl-6-t-butylphenol), 2,2'-propylidenebis(4-ethyl-6-t-butylphenol), 2,2'-propylidenebis(4-n-propyl-6-t-butylphenol), 2,2'-propylidenebis(4-i-propyl-6-t-butylphenol), 2,2'-propylidenebis(4-n-butyl-6-t-butylphenol), 2,2'-propylidenebis(4-i-butyl-6-t-butylphenol), 2,2'-propylidenebis(4,6-di-t-butylphenol), 2,2'-propylidenebis(4-t-pentyl-6-t-butylphenol), 2,2'-propylidenebis(4-nonyl-6-t-butylphenol), 2,2'- propylidenebis(4-t-octyl-6-t-butylphenol), 2,2'-propylidenebis(4-methyl-6-t-pentylphenol), 2,2'-propylidenebis(4-methyl-6-cyclohexylphenol), 2,2'-propylidenebis[4-methyl-6-(α-methylcyclohexyl)phenol)], 2,2'-propylidenebis(4-methyl-6-nonylphenol), 2,2'-propylidenebis(4-methyl-6-t-octylphenol), 2,2'-propylidenebis(4,6-di-t-pentylphenol), 2,2'-propylidenebis[4-nonyl-6-(α-methylbenzyl)phenol], 2,2'-propylidenebis[4-nonyl-6-(α,α-dimethylbenzyl)phenol], 2,2'-butylidenebis(4-methyl-6-t-butylphenol), 2,2'-butylidenebis(4-ethyl-6-t-butylphenol), 2,2'-butylidenebis(4,6-di-t-butylphenol), 2,2'-butylidenebis(4-methyl-6-cyclohexylphenol), 2,2'-butylidenebis[4-methyl-6-(α-methylcyclohexyl)phenol)], 2,2'-butylidenebis(4,6-di-t-pentylphenol), 2,2'-i-butylidenebis(4-methyl-6-t-butylphenol), 2,2'-i-butylidenebis(4-ethyl-6-t-butylphenol), 2,2'-i-butylidenebis(4,6-di-t-butylphenol), 2,2'-i-butylidenebis(4-methyl-6-cyclohexylphenol), 2,2'-i-butylidenebis[4-methyl-6-(α-methylcyclohexyl)phenol)], 2,2'-i-butylidenebis(4,6-di-t-pentylphenol), 2,2'-i-pentylidenebis(4-methyl-6-t-butylphenol), 2,2'-i-pentylidenebis(4-ethyl-6-t-butylphenol), 2,2'-i-pentylidenebis(4,6-di-t-butylphenol), 2,2'-i-pentylidenebis(4-methyl-6-cyclohexylphenol), 2,2'-pentylidenebis[4-methyl-6-(α-methylcyclohexyl)phenol)], 2,2'-pentylidenebis(4,6-di-t-pentylphenol), biphenyl-2,2'-diol, 3,3',5,5'-tetra-t-butylbiphenyl-2,2'-diol and 1,1'-binaphthyl-2,2'-diol.

The bisphenol of formula (III) can be produced by condensing an alkylphenol according to a known method described, for example, in JP-A-52-122350, U.S. Pat. No. 2,538,355 or JP-B-2-47451. An alkylphenol which are commercially available can also be used.

The alcohol (IV) as another starting material can be produced by reacting a corresponding carboxylic acid represented by the following formula (V):

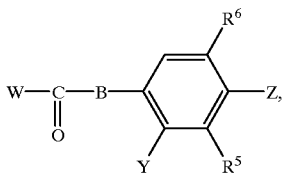

(V)

wherein $R^5$, $R^6$, Y and Z are as defined above; and W represents a hydroxyl group, a lower alkoxy group or a halogen atom with a corresponding aminoalcohol represented by the following formula (VI):

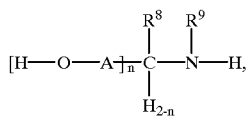

(VI)

wherein n, $R^8$, $R^9$ and A are as defined above, according to a conventional method under the coexistence of dicyclocarbodiimide, N,N-carbonyldiimidazole, phosphorous oxychloride, titanium tetrachloride, lithium amide, dibutyltin oxide and dimethylaluminum amide, if necessary.

Furthermore, the amino alcohols (VI) can be produced according to a known method described, for example, in Soviet Patent No. 1203083 and French Patent No. 2577242.

Examples of the alcohol (IV) include N-(2-hydroxyethyl)-2-hydroxy-3-t-butylbenzamide, N-(2-hydroxyethyl)-4-hydroxy-3-t-butylbenzamide, N-(2-hydroxyethyl)-2-hydroxy-3-t-butyl-5-methylbenzamide, N-(2-hydroxyethyl)-4-hydroxy-3-t-butyl-5-methylbenzamide, N-(2-hydroxyethyl)-2-hydroxy-3,5-di-t-butylbenzamide, N-(2-hydroxyethyl)-4-hydroxy-3,5-di-t-butylbenzamide, N-(2-hydroxyethyl)-3-(2-hydroxy-3-t-butylphenyl)propionamide, N-(2-hydroxyethyl)-3-(4-hydroxy-3-t-butylphenyl)propionamide, N-(2-hydroxyethyl)-3-(2-hydroxy-3-t-butyl-5-methylphenyl)propionamide, N-(2-hydroxyethyl)-3-(4-hydroxy-3-t-butyl-5-methylphenyl)propionamide, N-(2-hydroxyethyl)-3-(2-hydroxy-3,5-di-t-butylphenyl)propionamide, N-(2-hydroxyethyl)-3-(4-hydroxy-3,5-di-t-butylphenyl)propionamide, N-methyl-N-(2-hydroxyethyl)-3-(2-hydroxy-3-t-butylphenyl)propionamide, N-methyl-N-(2-hydroxyethyl)-3-(4-hydroxy-3-t-butylphenyl)propionamide, N-methyl-N-(2-hydroxyethyl)-3-(2-hydroxy-3-t-butyl-5-methylphenyl)propionamide, N-methyl-N-(2-hydroxyethyl)-3-(4-hydroxy-3-t-butyl-5-methylphenyl)propionamide, N-methyl-N-(2-hydroxyethyl)-3-(2-hydroxy-3,5-di-t-butylphenyl)propionamide, N-methyl-N-(2-hydroxyethyl)-3-(4-hydroxy-3,5-di-t-butylphenyl)propionamide, N-ethyl-N-(2-hydroxyethyl)-3-(2-hydroxy-3-t-butylphenyl)propionamide, N-ethyl-N-(2-hydroxyethyl)-3-(4-hydroxy-3-t-butylphenyl)propionamide, N-ethyl-N-(2-hydroxyethyl)-3-(2-hydroxy-3-t-butyl-5-methylphenyl)propionamide, N-ethyl-N-(2-hydroxyethyl)-3-(4 -hydroxy-3-t-butyl-5-methylphenyl)propionamide, N-ethyl-N-(2-hydroxyethyl)-3-(2-hydroxy-3,5-di-t-butylphenyl)propionamide, N-ethyl-N-(2-hydroxyethyl)-3-(4-hydroxy-3,5-di-t-butylphenyl)propionamide, N-t-butyl-N-(2-hydroxyethyl)-3-(2-hydroxy-3-t-butylphenyl)propionamide, N-t-butyl-N-(2-hydroxyethyl)-3-(4-hydroxy-3-t-butylphenyl)propionamide, N-t-butyl-N-(2-hydroxyethyl)-3-(2-hydroxy-3-t-butyl-5-methylphenyl)propionamide, N-t-butyl-N-(2-hydroxyethyl)-3-(4-hydroxy-3-t-butyl-5-methylphenyl)propionamide, N-t-butyl-N-(2-hydroxyethyl)-3-(2-hydroxy-3,5-di-t-butylphenyl)propionamide, N-t-butyl-N-(2-hydroxyethyl)-3-(4-hydroxy-3,5-di-t-butylphenyl)propionamide, N-(3-hydroxypropyl)-3-(2-hydroxy-3-t-butylphenyl)propionamide, N-(3-hydroxypropyl)-3-(4-hydroxy-3-t-butylphenyl)propionamide, N-(3-hydroxypropyl)-3-(2-hydroxy-3-t-butyl-5-methylphenyl)propionamide, N-(3-hydroxypropyl)-3-(4-hydroxy-3-t-butyl-5-methylphenyl)propionamide, N-(3-hydroxypropyl)-3-(2-hydroxy-3,5-di-t-butylphenyl)propionamide, N-(3-hydroxypropyl)-3-(4-hydroxy-3,5-di-t-butylphenyl)propionamide, N-(4-hydroxybutyl)-3-(2-hydroxy-3-t-butylphenyl)propionamide, N-(4-hydroxybutyl)-3-(4-hydroxy-3-t-butylphenyl)propionamide, N-(4-hydroxybutyl)-3-(2-hydroxy-3-t-butyl-5-methylphenyl)propionamide, N-(4-hydroxybutyl)-3-(4-hydroxy-3-t-butyl-5-methylphenyl)propionamide, N-(4-hydroxybutyl)-3-(2-hydroxy-3,5-di-t-butylphenyl)propionamide, N-(4-hydroxybutyl)-3-(4-hydroxy-3,5-di-t-butylphenyl)propionamide, N-(6-hydroxyhexyl)-3-(2-hydroxy-3-t-butylphenyl)propionamide, N-(6-hydroxyhexyl)-3-(4-hydroxy-3-t-butylphenyl)propionamide, N-(6-hydroxyhexyl)-3-(2-hydroxy-3-t-butyl-5-methylphenyl)propionamide, N-(6-hydroxyhexyl)-3-(4-hydroxy-3-t-butyl-5-methylphenyl)propionamide, N-(6-hydroxyhexyl)-3-(2-hydroxy-3,5-di-t-butylphenyl)propionamide, N-(6-hydroxybutyl)-3-(4-hydroxy-3,5-di-t-butylphenyl)propionamide, N-[1-(hydroxymethyl)-1-methyl-2-hydroxyethyl]-2-hydroxy-3-t-butylbenzamide, N-[1-(hydroxymethyl)-1-methyl-2-hydroxyethyl]-4- hydroxy-3-t-butylbenzamide, N-[1-(hydroxymethyl)-1-methyl-2-hydroxyethyl]-2-hydroxy-3-t-butyl-5-methylbenzamide, N-[1-(hydroxymethyl)-1-methyl-2-hydroxyethyl]-4-hydroxy-3-t-butyl-5-methylbenzamide, N-[1-(hydroxymethyl)-1-methyl-2-hydroxyethyl]-2-hydroxy-3,5-di-t-butylbenzamide, N-[1-(hydroxymethyl)-1-methyl-2-hydroxyethyl]-4-hydroxy-3,5-di-t-butylbenzamide, N-[1-(hydroxymethyl)-1-methyl-2-hydroxyethyl]-3-(2-hydroxy-3-t-butylphenyl)propionamide, N-[1-(hydroxymethyl)-1-methyl-2-hydroxyethyl]-3-(4-hydroxy-3-t-butylphenyl)propionamide, N-[1-(hydroxymethyl)-1-methyl-2-hydroxyethyl]-3-(2-hydroxy-3-t-butyl-5-methylphenyl)propionamide, N-[1-(hydroxymethyl)-1-methyl-2-hydroxyethyl]-3-(4-hydroxy-3-t-butyl-5-methylphenyl)propionamide, N-[1-(hydroxymethyl)-1-methyl-2-hydroxyethyl]-3-(2-hydroxy-3,5-di-t-butylphenyl)propionamide, N-[1-(hydroxymethyl)-1-methyl-2-hydroxyethyl]-3-(4-hydroxy-3,5di-t-butylphenyl)propionamide, N-methyl-N-[1-(hydroxymethyl)-1-methyl-2-hydroxyethyl]-3-(2-hydroxy-3-t-butylphenyl)propionamide, N-methyl-N-[1-(hydroxymethyl)-1-methyl-2-hydroxyethyl]-3-(4-hydroxy-3-t-butylphenyl)propionamide, N-methyl-N-[1-(hydroxymethyl)-1-methyl-2-hydroxyethyl]-3-(4-hydroxy-3-t-butylphenyl)propionamide, N-methyl-N-[1-(hydroxymethyl)-1-methyl-2-hydroxyethyl]-3-(2-hydroxy-3-t-butyl-5-methylphenyl)propionamide, N-methyl-N-[1-(hydroxymethyl)-1-methyl-2-hydroxyethyl]-3-(4-hydroxy-3-t-butyl-5-methylphenyl)propionamide, N-methyl-N-[1-(hydroxymethyl)-1-methyl-2-hydroxyethyl]-3-(2-hydroxy-3,5-di-t-butylphenyl)propionamide, N-methyl-N-[1-(hydroxymethyl)-1-methyl-2-hydroxyethyl]-3-(4-hydroxy-3,5-di-t-butylphenyl)propionamide, N-ethyl-N-[1-(hydroxymethyl)-1-methyl-2-hydroxyethyl]-3-(2-hydroxy-3-t-butylphenyl)propionamide, N-ethyl-N-[1-(hydroxymethyl)-1-methyl-2-hydroxyethyl]-3-(4-hydroxy-3-t-butylphenyl)propionamide, N-ethyl-N-[1-(hydroxymethyl)-1-methyl-2-hydroxyethyl]-3-(2-hydroxy-3-t-butyl-5-methylphenyl)propionamide, N-ethyl-N-[1-(hydroxymethyl)-1-methyl-2-hydroxyethyl]-3-(4-hydroxy-3-t-butyl-5-methylphenyl)propionamide, N-ethyl-N-[1-(hydroxymethyl)-1-methyl-2-hydroxyethyl]-3-(2-hydroxy-3,5-di-t-butylphenyl)propionamide, N-ethyl-N-[1-(hydroxymethyl)-1-methyl-2-hydroxyethyl]-3-(4-hydroxy-3,5-di-t-butylphenyl)propionamide, N-t-butyl-N-[1-(hydroxymethyl)-1-methyl-2-hydroxyethyl]-3-(2-hydroxy-3-t-butylphenyl)propionamide, N-t-butyl-N-[1-(hydroxymethyl)-1-methyl-2-hydroxyethyl]-3-(4-hydroxy-3 -t-butylphenyl)propionamide, N-t-butyl-N-[1-(hydroxymethyl)-1-methyl-2-hydroxyethyl]-3-(2-hydroxy-3-t-butyl-5-methylphenyl)propionamide, N-t-butyl-N-[1-(hydroxymethyl)-1-methyl-2-hydroxyethyl]-3-(4-hydroxy-3-t-butyl-5-methylphenyl)propionamide, N-t-butyl-N-[1-(hydroxymethyl)-1-methyl-2-hydroxyethyl]-3-(2-hydroxy-3,5-di-t-butylphenyl)propionamide, N-t-butyl-N-[1-(hydroxymethyl)-1-methyl-2-hydroxyethyl]-3-(4-hydroxy-3,5-di-t-butylphenyl)propionamide, N-[1-(hydroxymethyl)-1-ethyl-2-hydroxyethyl]-2-hydroxy-3-t-butylbenzamide, N-[1-(hydroxymethyl)-1-ethyl-2-hydroxyethyl]-4-hydroxy-3-t-butylbenzamide, N-[1-(hydroxymethyl)-1-ethyl-2-hydroxyethyl]-2-hydroxy-3-t-butyl-5-methylbenzamide, N-[1-(hydroxymethyl)-1-ethyl-2-hydroxyethyl]-4-hydroxy-3-t-butyl-5-methylbenzamide, N-[1-(hydroxymethyl)-1-ethyl-2-hydroxyethyl]-2-hydroxy-3,5-di-t-butylbenzamide, N-[1-(hydroxymethyl)-1-ethyl-2-hydroxyethyl]-4-hydroxy-3,5-di-t-butylbenzamide, N-[1-(hydroxymethyl)-1-ethyl-2-hydroxyethyl]-3-(2-hydroxy-3-t-butylphenyl)propionamide, N-[1-(hydroxymethyl)-1-ethyl-2-hydroxyethyl]-3-(4-hydroxy-3-t-butylphenyl)propionamide, N-[1-(hydroxymethyl)-1-ethyl-2-hydroxyethyl]-3-(2-hydroxy-3-t-butyl-5-methylphenyl)propionamide, N-[1-(hydroxymethyl)-1-ethyl-2-hydroxyethyl]-3-(4-hydroxy-3-t-butyl-5-methylphenyl)propionamide, N-[1-(hydroxymethyl)-1-ethyl-2-hydroxyethyl]-3-(2-hydroxy-3,5-di-t-butylphenyl)propionamide, N-[1-(hydroxymethyl)-1-ethyl-2-hydroxyethyl]-3-(4-hydroxy-3,5-di-t-butylphenyl)propionamide, N-methyl-N-[1 -(hydroxymethyl)-1-ethyl-2-hydroxyethyl]-3-(2-hydroxy-3-t-butylphenyl)propionamide, N-methyl-N-[1-(hydroxymethyl)-1-ethyl-2-hydroxyethyl]-3-(4-hydroxy-3-t-butylphenyl)propionamide, N-methyl-N-[1-(hydroxymethyl)-1-ethyl-2-hydroxyethyl]-3-(2-hydroxy-3-t-butyl-5-methylphenyl)propionamide, N-methyl-N-[1-(hydroxymethyl)-1-ethyl-2-hydroxyethyl]-3-(4-hydroxy-3-t-butyl-5-methylphenyl)propionamide, N-methyl-N-[1-(hydroxymethyl)-1-ethyl-2-hydroxyethyl]-3-(2-hydroxy-3,5-di-t-butylphenyl)propionamide, N-methyl-N-[1-(hydroxymethyl)-1-ethyl-2-hydroxyethyl]-3-(4-hydroxy-3,5-di-t-butylphenyl)propionamide, N-ethyl-N-[1-(hydroxymethyl)-1-ethyl-2-hydroxyethyl]-3-(2-hydroxy-3-t-butylphenyl)propionamide, N-ethyl-N-[1-(hydroxymethyl)-1-ethyl-2-hydroxyethyl]-3-(4-hydroxy-3-t-butylphenyl)propionamide, N-ethyl-N-[1-(hydroxymethyl)-1-ethyl-2-hydroxyethyl]-3-(2-hydroxy-3-t-butyl-5-methylphenyl)propionamide, N-ethyl-N-[1-(hydroxymethyl)-1-ethyl-2-hydroxyethyl]-3-(4-hydroxy-3-t-butyl-5-methylphenyl)propionamide, N-ethyl-N-[1-(hydroxymethyl)-1-ethyl-2-hydroxyethyl]-3-(2-hydroxy-3,5-di-t-butylphenyl)propionamide, N-ethyl-N-[1-(hydroxymethyl)-1-ethyl-2-hydroxyethyl]-3-(4-hydroxy-3,5-di-t-butylphenyl)propionamide, N-t-butyl-N-[1-(hydroxymethyl)-1-ethyl-2-hydroxyethyl]-3-(2-hydroxy-3-t-butylphenyl)propionamide, N-t-butyl-N-[1-(hydroxymethyl)-1-ethyl-2-hydroxyethyl]-3-(4-hydroxy-3-t-butylphenyl)propionamide, N-t-butyl-N-[1-(hydroxymethyl)-1 ethyl-2-hydroxyethyl]-3-(2-hydroxy-3-t-butyl-5-methylphenyl)propionamide, N-t-butyl-N-[1-(hydroxymethyl)-1-ethyl-2-hydroxyethyl]-3-(4-hydroxy-3-t-butyl-5-methylphenyl)propionamide, N-t-butyl-N-[1-(hydroxymethyl)-1-ethyl-2-hydroxyethyl]-3-(2-hydroxy-3,5-di-t-butylphenyl)propionamide and N-t-butyl-N-[1-(hydroxymethyl)-1-ethyl-2-hydroxyethyl]-3-(4-hydroxy-3,5-di-t-butylphenyl)propionamide.

The hydrolysis resistance of the phosphites (I) of the present invention can be improved by containing an amine, an acid-bonded metal salt and the like.

Examples of the amine include trialkanolamines such as triethanolamine, tripropanolamine, tri-i-propanolamine and the like; dialkanolamines such as diethanolamine, dipropanolamine, di-i-propanolamine, tetraethanolethylenediamine, tetra-i-propanolethylenediamine and the like; monoalkanolamines such as dibutylethanolamine, dibuty-i-propanolamine and the like; aromatic amines such as 1,3,5-trimethyl-2,4,6-triazine and the like; alkylamines such as dibutylamine, piperidine, 2,2,6,6,-tetramethylpiperidine, 4-hydroxy-2,2,6,6-tetramethylpiperidine and the like; polyalkylenepolyamines such as hexamethylenetetramine, triethylenediamine, triethylenetetraimine, tetraethylenepentamine and the like; and hindered amine photostabilizers described hereinafter.

Furthermore, there can also be used a long-chain aliphatic amine described in JP-A-61-63586, a compound having a steric hindrance amine group described in JP-A-6-329830, a hindered piperidinyl photostabilizer described in JP-A-7-90270 and an organic amine described in JP-A-7-278164.

A proportion of the amine to be used is normally about 0.01 to 25% by weight based on the phosphites (I).

Typical examples of the acid-bonded metal salt include hydrotalcites. Examples of the hydrotalcites include double salt compounds represented by the following formula:

$$M^{2+}_{1-x} \cdot M^{3+}_{x} \cdot (OH^-)_2 \cdot (A^{n-})_{x/n} \cdot pH_2O$$

wherein $M^{2+}$ represents Mg, Ca, Sr, Ba, Zn, Pb, Sn and/or Ni; $M^{3+}$ represents Al, B or Bi; n represents a numerical value of 1 to 4; x represents a number of 0 to 0.5; p represents a number of 0 to 2; and $A^{n-}$ represents an anion having a valency of n.

Specific examples of the amino having a valence of n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, $-OOCCOO-$, $(CHOHCO)_2^{2-}$, $C_2H_4(COO)_2^{2-}$, $(CH_2COO)_2^{2-}$, $CH_3CHOHCOO-$, $SiO_3^{2-}$, $SiO_4^{4-}$, $Fe(CN_6^{4-}$, $BO_3^{3-}$, $PO_3^{3-}$ and $HPO_4^{2-}$.

Particularly preferred double salt compounds represented by the above formula include hydrotalcites represented by the following formula:

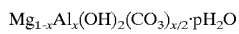

$$Mg_{1-x}Al_x(OH)_2(CO_3)_{x/2} \cdot pH_2O$$

wherein x and p are as defined above.

The hydrotalcites may be natural or synthetic products, and can be used regardless of crystal structure and crystal particle diameter thereof.

Furthermore, an ultrafine zinc oxide described in JP-A-6-329830 and an inorganic compound described in JP-A-7-278164 can also be used.

A proportion of the acid-bonded metal salt to be used is normally about 0.01 to 25% by weight based on the phosphites (I).

The phosphites (I) of the present invention are effective for stabilizing an organic material against heat deterioration and oxidization deterioration. Examples of the organic material which can be stabilized by phosphites (I) of the present invention include the following:

(1) polyethylene, for example, high-density polyethylene (HD-PE), low-density polyethylene (LD-PE) and linear low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystyrenes, for example, polystyrene, poly(p-methylstyrene) and poly(α-methylstyrene)
(7) As (acrylonitrile/styrene copolymer) resin
(8) ABS (acrylonitrile/butadiene/styrene copolymer) resin
(9) AAS (special acrylic rubber/acrylonitrile/styrene copolymer) resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14) etyhylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint
(52) wax, and
(53) lubricating oil.

The organic materials can be stabilized alone or in combination thereof. The organic materials which can be stabilized by phosphites (I) of the present invention are not limited to the organic materials exemplified above. Among them, the thermoplastic resin, particularly polyolefin such as polyethylene (e.g. HD-PE, lD-PE, LIDPE, etc.) and polyolefin (e.g. polypropylene, etc.), and the engineering resin such as polyamide, polyethylene terephthalate, polybutylene terephthalate and polycarbonare, are more suitable to be stabilized by phosphites (I) of the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a π or σ bond, halogenated compound, alcolate, ester, aryl and the like, and these complexes may be used as it is, or a base material such as magnesium chloride, titanium chloride, alumina, silicon oxide, etc., may carry the complexes.

As the polyolefin, for example, there are preferably used those produced by using Ziegler-Natta catalyst, TNZ catalyst, metallocene catalyst, Phillips catalyst and the like.

Also the engineering resin is not specifically limited. The polyamide resin may be those which have an amide bond at the polymer chain and can be molten with heating. For example, they may be produced by any method such as condensation reaction between diamines and dicarboxylic acids, condensation reaction of aminocarboxylic acids and ring opening polymerization of lactams. Typical examples thereof include nylon 66, nylon 69, nylon 610, nylon 612, poly-bis(p-aminocyclohexyl)methanedodecamide, nylon 46, nylon 6, nylon 12 and copolymers (e.g. nylon 66/6 as a copolymer of nylon 66 and nylon 6, nylon 6/12, etc.).

The polyester resin may be those which have an ester bond at the polymer chain and can be molten with heating. Examples thereof include polyester obtained by the polycondensation between dicarboxylic acids and a dihydroxy compound. The polyester may be a homopolyester or a copolyester.

The polycarbonate may be those which have a carbonate bond at the polymer chain and can be molten with heating. Examples thereof include polycarbonate obtained by reacting an aromatic hydroxy compound and/or a small amount of polyhydroxy compound with a carbonate precursor such as phosgene, diphenyl carbonate. etc. in the presence of a solvent, an acid receptor and a molecular weight adjustor. The polycarbonate resin may be straight-chain or branched resin, or may be a copolymer.

When the organic material is stabilized by containing the phophites (I) of the present invention, the phosphites (I) are normally formulated in an amount of about 0.01 to 5 parts by weight, preferably about 0.03 to 3 parts by weight, more preferably about 0.05 to 1 parts by weight, based on 100 parts by weight of the organic material. When the amount is less than 0.01 parts by weight, the stabilizing effect is not sufficient, necessarily. On the other hand, even when the amount exceeds 5 parts by weight, the improvement of the effect corresponding to the amount is not obtained and it is economically disadvantageous.

When the phosphites (I) of the present invention are contained in the organic material, if necessary, there can also be contained other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, antistatic agent, pigment, filler, pigment, anti-blocking agent, surfactant, processing aid, foaming agent, emulsifier, brightener, calcium stearate, neutralizing agent (e.g. hydrotalcite, etc.), coloring modifier (e.g. 9,10-dihydro-oxa-10-phosphophenanthrene-10-oxide, etc.) and co-stabilizer (e.g. benzofurans, indolines, etc. described in U.S. Pat. Nos. 4,325,853, 4,338,244, 5,175,312, 5,216,053, 5,252,643 and 4,316,611, DE-A-4,316,622 and 4,316,876, and EP-A-589, 839 and 591,101). These additives can be formulated together with the phosphities (I), and also be formulated in the stage other than the stage where the phosphites (I) are formulated.

Examples of the phenol antioxidant include the followings.

(1) Examples of alkylated monophenol 2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof.

(3) Examples of hydroquinone and alkylated hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a mixture thereof.

(4) Examples of tocopherol

α-tocopherol, β-tocopherol, γ-tocopherol, δ-tocopherol and a mixture thereof.

(5) Examples of hydroxylated thiodiphenyl ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like.

(6) Examples of alkylidenebisphenol and derivative thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol)], 2,2'-methylenebis(4-methyl-6-cyclohexylphenol), 2,2'-methylenebis(4-methyl-6-nonylphenol), 2,2'-methylenebis(4,6-di-t-butylphenol)], 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α,α-dimethylbenzyl)-4-nonylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis[3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis-3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O-, N- and S-benzyl derivative 3,5,3',5'-tetra-t-butyl-4,4'-dihydroxydibenzyl ether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and a mixture thereof.

(8) Examples of hydroxybenzylated malonate derivative dioctadecyl-2,2-bis(3,5-di-t-butyl-2-hydroxybenzyl) malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof.

(9) Examples of aromatic hydroxybenzyl derivative 1,3,5-trimethyl-2,4,6-tris(3,5-di-t-butyl-4-hydroxybenzyl)benzene, 1,4-bis(3,5-di-t-butyl-4- hydroxybenzyl)- 2,3,5,6-tetramethylbenzene, 2,4,6-tris(3,5-t-butyl-4-hydroxybenzyl)phenol and a mixture thereof.

(10) Examples of triazine derivative 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate and a mixture thereof.

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof.

(12) Examples of acylaminophenol derivative anilide 4-hydroxylaurate, anilide 4-hydroxystearate, octyl-N-(3,4-di-t-butyl-4-hydroxyphenyl)carbanate and a mixture thereof.

(13) Ester of β-(3,5-di-t-butyl-4-hydroxyphenyl) propionic acid and the following monhydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(14) Ester of β-(5-t-butyl-4-hydroxy-3-methylphenyl) propionic acid and the following monhydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(15) Ester of β-(3,5-dicyclohexyl-4-hydroxyphenyl) propionic acid and the following monhydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(16) Ester of 3,5-t-butyl-4-hydroxyphenylacetic acid and the following monhydric or polyhydric alcohol:

methanol, ethanol, octanol, octadecanol, ethylene glycol, 1,3-propanediol, 1,4-butanediol, 1,6-hexanediol, 1,9-nonanediol, neopentyl, glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(17) Examples of amide of β-(3,5-di-t-butyl-4-hydroxyphenyl)propionic acid and the following amine:

N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, N,N'-bis[3-(3',5'-di-t-butyl-4'-hydroxyphenyl)propionyl]trimethylenediamine and a mixture thereof.

Examples of the sulfur antioxidant include the followings:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate and neopentanetetraylkis(3-lauryl thiopropionate).

Examples of the phosphorous antioxidant include the followings:

triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl) pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, bis (2,4,6-tri-t-butylphenyl)pentaerythritol diphosphate, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis (2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2', 2"-nitrilo[triethyl-tris(3,3',5,5'-tetra-t-butyl-1,1'-biphenyl-2, 2'-diyl)phosphite and a mixture thereof.

Examples of the ultraviolet absorber include the followings:

(1) Examples of salicylate derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3', 5'-di-t-butyl-4'-hydroxybenzoate, 2-methyl-4,6-di-t-butylphenyl 3',5'-di-t-butyl-4'-hydroxybenzoate and a mixture thereof.

(2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and a mixture thereof.

(3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy)

carbonylethyl]-2'-hydroxyphenyl]-5-chlorobenzotriazole, 2-[3'-t-butyl-2'-hydroxy-5'-(2-methoxycarbonylethyl) phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6 -tetrahydrophthalimidemethyl)-5-methylphenyl]benzotriazole, 2-(3',5'-di-t-butyl-2'-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl) phenyl]benzotriazole, 2,2'-methylenebis[6-(2H-benzotriazole-2-yl)-4-(1,1,3,3-tetramethylbutyl)phenol, 2,2'-methylenebis[4-t-butyl-6-(2H-benzotriazol-2-yl) phenol], condensate of poly(3–11)(ethylene glycol) and 2-[3'-t-butyl-2'-hydroxy-5'-(2-methoxycarbonylethyl) phenyl]benzotriazole, condensate of poly(3–11)(ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl] propioinate, octyl 3-(3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl] propionate, 3-[3-t-butyl-5-(5-chloro-2H-benzotriazol-2-yl)-4-hydroxyphenyl]propionic acid and a mixture thereof.

(1) Examples of the photostabilizer include the followings.

(1) Examples of hindered amine photostabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-penatmethyl-4-piperidyl decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-buty-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6,-tetramethyl-4-piperidyl) propionamide, tetarkis(2,2,6,6-tetramethyl-4-piperidyl) 1,2,3,4-butaneteracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1,1,3,3-tetramethylbutyl)imino- 1,3,5-triazin-2,4-diyl ((2,2,6,6-tetramethyl-4-piperidyl)imino)hexamethylene ((2,2,6,6-tetramethyl-4-piperidyl)imino)], polycondensate of N,N'-bis(2,2,6,6-tetramethyl-4-piperidyl)hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N', 4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof.

(2) Examples of acrylate photostabilizer ethyl α-cyano-β, β-diphenylacrylate, isooctyl α-cyano-β, β-diphenylacrylate, methyl α-carbomethoxycinnamate, methyl α-cyano-β-methyl-methoxycinnamate, buty α-cyano-β-methyl-p-methoxycinnamate, methyl α-carbomethoxy-p-methoxycinnamate and N-(β-carbomethoxy-β-cyano-vinyl)-2-methylindoline and a mixture thereof.

(3) Examples of nickel photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof.

(4) Examples of oxamide photostabilizer 4,4'-dioctyloxyoxanilide, 2,2'-diethoxyoxanilide, 2,2'-dioctyloxy- 5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and a mixture thereof.

(5) Examples of 2-(2-hydroxyphenyl)-1,3,5-triazine photostabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the metal inactivating agent include the followings:

N,N'-diphenyloxamide, N-salicylal-N'-salicyloylhydrazine, N,N'-bis(salicyloyl)hydrazine, N,N'-bis(3,5,-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoyl-bisphenyl hydrazide, N,N'-bis(salicyloyl)thiopropionyl dihydrazide and a mixture thereof.

Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis(β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, resin derivative and the like.

Examples of the nucleating agent include the followings: sodium 2,2'-methylenebis(4,6-di-t-butylphenyl) phosphate, [phosphoric acid-2,2'-methylenebis(4,6-di-t-butylphenyl)] dihydroxyaluminum, bis[phosphoric acid-2, 2'-methylenebis(4,6-di-t-butylphenyl)] dihydroxyaluminum, tris[phosphoric acid-2,2'-methylenebis (4,6-di-t-butylphenyl)] aluminum, sodium bis(4,6-di-t-butylphenyl)phosphate, benzoic acid metal salt such as sodium benzoate, aluminum p-t-butylbenzoate, 1,3:2,4-bis (O-benzylidene)sorbitol, 1,3:2,4-bis(O-ethylbenzylidene) sorbitol, 1,3:2,4-bis(O-methylbenzylidene)sorbitol, 1,3-O-3,4-dimethylbenzylidene-2,4-O-benzylidenesorbitol, 1,3-O-benzylidene-2,4-O-3,4-dimethylbenzylidene sorbitol, 1,3:2, 4-bis(O-3,4-dimethylbenzylidene)sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaoline, mica, barium sulfate, carbon black, carbon fiber, zeolite and a mixture thereof.

Among these additives above, phenol antioxidant, phosphorous antioxidant, ultraviolet absorber, hindered amine photostabilizer, peroxide scavenger and neutrializing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis[4-ethyl-6-t-butylphenol), 2,2'-methylenebis(4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-mbutylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris (5-t-butyl-4-hydroxy-2-methylphenyl)butane, ethylene glycol, bis[3,3-bis-3'-t-butyl-4'-hydroxyphenyl)butyrate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, calcium salt a of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5- trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl-4-hydroxy-3-methylcinnamate), 3,9-bis[2-(3-(3-t-butyl-4-hydroxy-5-methylphenyl) propionyloxy)-1,1-dimethylethyl]-2,4,8,10-tetraoxaspiro [5.5] undecane, N,N'-bis[3-(3',5'-di-t-butyl-4'-hydroxyphenyl) propionyl] hydrazine and N,N'-bis[3-(3',5'-di-t-butyl-4'-hydroxyphenyl)propionyl]hexamethylenediamine.

Examples of the particularly preferred phosphorous antioxidant include the followings, and they may be used in combination of the two or more:

tris(nonylphenyl)phosphite, tris(2,4-di-t-butylphenyl) phosphite, distearyl pentaerythritol diphosphite, bis(2, 4-di-t-butylphenyl)pentaerythritol diphosphite, bis(2,4-di-t-butyl-6-methylphenyl)pentaerythritol diphosphite, bis(2,6-di-t-butyl-4-methylphenyl) pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis (4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholilnane and 2,2',2"-nitrilo[triethyl-tris(3,3',5,5'-tetra-t-butyl-1, 1'-biphenyl-2,2'-diyl) phosphite.

Examples of the particularly preferred ultraviolet absorber include the followings, and two or more kinds of them can be used.

phenyl salicylate, 4-t-butylphenyl salicylate, 2,4-di-t-butylphenyl 3,'5'-di-t-butyl-4'-hydroxybenzoate, 4-t-octylphenyl salycilate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl) benzotriazole, 2-(3',5'-di-t-butyl-2'-hydroxyphenyl) benzotriazole, 2-(5'-t-butyl-2'-hydroxyphenyl) benzotriazole, 2-(2'-hydroxy=5'-t-octylphenyl) benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl) benzotriazole, 2-(3',5'-di-t-amyl-2'-hydroxyphenyl) benzotriazole and 2-[2'-hydroxy-3',5'-bis(α,α-dimethylbenzyl) phenyl]-2H-benzotriazole.

Examples of the particularly preferred photostablizer include the followings, and two or more kinds of them can be used.

bis(2,2,6,6-tetramethyl-4-piperidyl)sebacate, bis(1,2,2,6, 6-pentamethyl-4-piperidyl)sebacate, bis(N-oxtoxy-2,2, 6,6-pentamethyl-4-piperidyl) sebacate, bis(N-octoxy-2,2,6,6-pentamethyl-4-piperidyl) sebacate, bis(N-benzyloxy-2,2,6,6-tetarmethyl-4-piperidyl) sebacate, bis(N-cyclohexyloxy-2,2,6,6-tetramethyl-4-piperidyl) sebacate, bis(1,2,2,6,6-pentamethyl-4-piperidyl) 2-(3, 5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bis(2,2, 6,6-tetramethyl-4-piperidyl) succinate, 2,2,6,6-tetramethyl-4-piperidyl methacrylate, 4-[3-(3,5-di-t- butyl-4-hydroxyphenyl) propionyloxy)-1-[2-(3-(3,5-di-t-butyl-4-hydroxyphenyl) propionyloxy)ethyl]-2,2,6,6-tetramethylpiperidine, 2-methyl-2-(2,2,6,6-tetramethyl-4-piperidyl) amino-N-(2,2,6,6-tetarmethyl-4-piperidyl) propionamide, tetrakis(2,2,6,6-tetramethyl-4-piperidyl) 1,2,3,4-butanetetracarboxylate, tetrakis(1,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4,-butanetetracarboxylic acid and 2,2,6,6-tetramethyl-4-piperidinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl) imino)hexamethylene ((2,2,6,6-tetramethyl-4-piperidyl) imino)] and poly[(6-(1,1,3,3-tetramethylbutyl)-1,3,5-triazin-2,4-diyl ((2,2,6,6-tetramethyl-4-piperidyl) imino)hexamethylene ((2,2,6,6-tetramethyl-4-piperidyl) imino)].

For formulating the phosphites (I) and optionally used other additives in the organic material, known all methods and devices for obtaining a homogeneous mixture can be used. For example, when the organic material is a solid polymer, the phosphites (I) and other additives can be directly dry-blended in the solid polymer, or the phosphites (I) and other additives can also be formulated in the solid polymer in the form of a master-batch. When the organic material is a liquid polymer, the phosphites (I) and other additives can be formulated in the polymer solution during or immediately after polymerization in the form of a solution or a dispersion. On the other hand, when the organic material is a liquid such as oil, the phosphites (I) and other additives can also be dissolved by direct addition, or the phosphites (I) and other additives can also be added in the form of a solution of dispersion in a liquid medium.

The phosphites (I) of the present invention have excellent performance as a stabilizer for various organic materials such as thermoplastic resin (e.g. polyolefin, etc.), and the organic material containing this compound is stable to heat and oxidization on their production, processing and use. Therefore, high-quality product can be obtained.

The following Examples further illustrate the present invention in detail but are not to be construed to limit the scope thereof.

EXAMPLE 1

Production of 6-{2-[3-(4-hydroxy-3,5-di-tpbutylphenyl) propionamide]ethoxy}-2,10-dimethyl-4,8-di-t-butyl-12H-dibenzo [d,g][1,3,2]dioxaphosphosine (Compound 1)

In a flask equipped with a thermometer, a stirrer and a cooling condenser, 2,2'-methylenebis(6-t-butyl-4-methylphenol) (10.2 g) and toluene (150 ml) were charged under a nitrogen flow. After phosphorous trichloride (4.1 g) was added under stirring, triethylamine (6.4 g) was added thereto. Then, the resulting mixture was maintained at 80° C. for 4 hours.

After cooling the mixture to room temperature, toluene (50 ml) and N-(2-hydroethyl)-3-(4-hydroxy-3,5-di-t-butylphenyl) propionamide (9.6 g) were added and, then, triethylamine (3.2 g) was added, followed by maintaining the mixture at 80° C. for 10 hours.

After cooling the mixture to room temperature, the formed hydrochloride salt of triethylamine was filtered and washed. Then, the filtrate was concentrated and the residue was purified by silica gel chromatography to obtain 11 g of a white crystal.

Mass spectrometric analysis (FD-MS): m/z 689
$^1$H-NMR (CDCl$_3$)
1.35 (s, 18H), 1.45 (s, 18H), 2.3 (s, 6H), 2.5 (t, 2H), 2.9 (t, 2H), 3.4 (d, 1H), 3.7 (m, 2H), 4.3 (d, 1H), 4.5 (t, 2H), 5.1 (s, 1H), 6.1 (m, 1H), 7.0 (s, 4H), 7.1 (s, 2H)
$^{31}$P-NMR (CDCl$_3$)
128 ppm (s)

EXAMPLE 2

Production of 6-{2-[3-(4-hydroxy-3,5-di-t-butylphenyl) propionamide]ethoxy}-2,3,8,10-tetra-t-pentyl-12-methyl-dibenzo[d,g][1,3,2]dioxaphosphosine (Compound 2)

According to the same manner as that in Example 1 except for using 2,2'-ethylidenebis(4,6-di-t-pentylphenol) (14.8 g) in place of 2,2'-methylenebis(6-t-butyl-4-methylphenol), 8.7 g of a white crystal was obtained.

Mass spectrometric analysis (FD-MS): m/z 844
$^1$H-NMR (CDCl$_3$)
0.6 (t, 12H), 1.2–1.5 (m, 42H), 1.6 (d, 3H), 1.8 (q, 8H), 2.5 (t, 2H), 2.9 (t, 2H ), 3.7 (m, 2H), 4.5 (t, 2H), 4.8 (1H, q), 5.1 (s, 1H), 6.1 (m, 1H), 7.0 (s, 2H), 7.1 (s, 2H), 7.3 (s, 2H)
$^{31}$P-NMR (CDCl$_3$)
127 ppm (s)

EXAMPLE 3

Production of 6-{2-[N-methyl-3-(4-hydroxy-3,5-di-t-butylphenyl) propionamide]ethoxy}-2,10-dimethyl-4,8-di-t-butyl-12H-dibenzo[d,g][1,3,2]dioxaphosphosine (Compound 3)

In a flask equipped with a thermometer, a stirrer and a cooling condenser, 2,2'-methylenebis(6-t-butyl-4-methylphenol) (8.5 g) and toluene (150 ml) were charged under a nitrogen flow. After phosphorous trichloride (3.4 g) was added under stirring, triethylamine (5.3 g) was added thereto. Then, the mixture was maintained at 80° C. for 4 hours.

After cooling the mixture to room temperature, toluene (50 ml) and N-methyl-N-(2-hydroxyethyl)-3-(4-hydroxy-3,5-di-t-butylphenyl) propionamide (8.4 g) were added and, then, triethylamine (2.7 g) was added, followed by maintaining the mixture at 80° C. for 11 hours.

After cooling the mixture to room temperature, the formed hydrochloride salt of triethylamine was filtered and washed. Then, the filtrate was concentrated and the residue was purified by silica gel chromatography to obtain 10.6 g of a white crystal.

Mass spectrometric analysis (FD-MS): m/z 703 Elemental analysis: phosphorous % 4.37 (Calcd. 4.40)

EXAMPLE 4

Production of 6-{2-[N-methyl-3-(4-hydroxy-3,5-di-t-butylphenyl) propionamide]ethoxy}-2,4,8,10-tetra-t-pentyl-12-methyl-dibenzo[d,g][1,3,2]dioxaphosphosine (Compound 4)

According to the same manner as that in Example 3 except for using 2,2'-ethylidenebis(4,6-di-t-pentylphenol)

(8.4 g) in place of 2,2'-methylenebis(6-t-butyl-4-methylphenol), 11.5 g of a white crystal was obtained.

Mass spectrometric analysis (FD-MS): m/z 858 Elemental analysis: phosphorous % 3.58 (Calcd. 3.61)

EXAMPLE 5

Production of N-{1,1-bis[(2,10-dimethyl-4,8-di-t-butyl-12H-dibenzo[d,g][1,3,2]dioxaphosphosine-6-yl)oxymethyl]ethyl}-3-(4-hydroxy-3,5-di-t-butylphenyl) propionamide (Compound 5)

In a flask equipped with a thermometer, a stirrer and a cooling condenser, 2,2'-methylenebis(6-t-butyl-4-methylphenol) (13.6 g) and toluene (150 ml) were charged under a nitrogen flow. After phosphorous trichloride (5.5 g) was added under stirring, triethylamine (8.5 g) was added thereto. Then, the mixture was maintained at 80° C. for 4 hours.

After cooling the mixture to room temperature, toluene (50 ml) and N-[1-(hydroxymethyl)-1-methyl-2-hydroxyethyl]-4-hydroxy-3,5-di-t-butylbenzamide (7.3 g) were added and, then, triethylamine (7.3 g) was added, followed by maintaining the mixture at 80° C. for 8 hours.

After cooling the mixture to room temperature, the formed hydrochloride salt of triethylamine was filtered and washed. Then, the filtrate was concentrated and the residue was purified by silica gel chromatography to obtain 123.2 g of a white crystal.

Mass spectrometric analysis (FD-MS): m/z 1102

$^1$H-NMR (CDCl$_3$)

1.4 (s, 54H), 1.7 (s, 3H), 2.3 (s, 12H), 2.5 (t, 2H), 2.9 (t, 2H), 3.4 (d, 2H), 4.3 (d, 2H), 4.8 (m, 4H ), 5.1 (s, 1H), 5.8 (s, 1H), 6.9 (s, 2H), 7.0 (s, 4H), 7.1 (s, 4H), $^{31}$P-NMR (CDCl$_3$)

128 ppm (s)

EXAMPLE 6

Production of N-{1,1-bis[(2,4,8,10-tetra-t-pentyl-12-methyl-12H-dibenzo[d,g][1,3,2]dioxaphosphosine-6-yl)oxymethyl]ethyl}-3-(4-hydroxy-3,5-di-t-butylphenyl) propionamide (Compound 6)

According to the same manner as that in Example 5 except for using 2,2'-ethylidenebis(4,6-di-t-pentylphenol) (19.8 g) in place of 2,2'-methylenebis(6-t-butyl-4-methylphenol), 12.8 g of a white crystal was obtained.

Mass spectrometric analysis (FD-MS): m/z 1411 Elemental analysis: phosphorous % 4.34 (Calcd. 4.39)

EXAMPLE 7

Thermal Stability Test of Polypropylene

| [Formulation] | |
|---|---|
| Polypropylene (block) | 100 Parts by weight |
| Calcium stearate | 0.05 Parts by weight |
| Test compound | 0.05 Parts by weight |

C-1: compound 1 (produced in Example 1)
C-2: compound 2 (produced in Example 2)
C-5: compound 5 (produced in Example 5)
P-1: 2,10-dimethyl-4,8-di-t-butyl-6-{2-[3-(3-t-butyl-4-hydroxy-5-methylphenyl) propionyloxy]ethoxy}-12H-dibenzo[d,g][1,3,2]dioxaphosphosine
P-2: 2,4,8, 10-tetra-t-pentyl-6-{2-[3-(3,5-di-t-butyl-4-hydroxyphenyl) propionyloxy]ethoxy}-12-methyl-12H-dibenzo [d,g][1,3,2]dioxaphosphosine Using a 30 mm φ monoaxial extruder, the above formulating materials were melt-kneaded at 250° C. to form pellets. Using a melt indexer, MFR (g/10 minutes) of the resulting pellets was measured at 250° C. under the conditions of a load of 2160 g and a retention time of 5 minutes. The results are shown in Table 1. The smaller the MFR value becomes, the better the processing stability.

TABLE 1

| | Example | | | Comparative Example | | |
|---|---|---|---|---|---|---|
| | 1 | 2 | 3 | 1 | 2 | 3 |
| Test compound | C-1 | C-2 | C-5 | — | P-1 | P-2 |
| Processing stability | 17.6 | 18 | 17.8 | 29.4 | 22.0 | 22.5 |

EXAMPLE 8

Thermal Stability Test of Linear Low-Density Polyethylene

| [Formulation] | |
|---|---|
| Unstabilized Linear Low-density polyethylene | 100 Parts by weight |
| Hydrotalcite | 0.1 Parts by weight |
| Test compound | 0.15 Parts by weight |

C-1; compound 1 (produced in Example 1)
C-2: compound 2 (produced in Example 2)
C-5: compound 5 (produced in Example 5)
P-1: 2,10-dimethyl-4,8-di-t-butyl-6-{2-[3-(3-t-butyl-4-hydroxy-5-methylphenyl) propionyloxy]ethoxy}-12H-dibenzo[d,g][1,3,2]dioxaphosphosine
P-2: 2,4,8,10-tetra-t-pentyl-6-{2-[3-(3,5-di-t-butyl-4-hydroxyphenyl) propionyloxy]ethoxy}-12-methyl-12H-dibenzo[d,g][1,3,2]dioxaphosphosine Using a 30 mm φ monoaxial extruder, the above formulating materials were melt-kneaded at 250° C. to form pellets. Using a laboplasto mill, the resulting pellets were kneaded at 240° C., 100 rpm under a nitrogen atmosphere and the time at which a torque value due to crosslinking becomes maximum (gel build-up time) was measured. The results are shown in Table 2. The longer the gel build-up time, the more the crosslinking on kneading is inhibited, which indicates excellent processing stability.

TABLE 2

| | Example | | | Comparative Example | | |
|---|---|---|---|---|---|---|
| | 1 | 2 | 3 | 1 | 2 | 3 |
| Test compound | C-1 | C-2 | C-5 | — | P-1 | P-2 |
| Processing stability | 33.0 | 27.0 | 28.0 | 5.0 | 16.5 | 17.0 |

EXAMPLE 9

Thermal Stability Test of Nylon

| [Formulation] | |
|---|---|
| Unstabilized nylon 6 | 100 Parts by weight |
| Test stabilizer | 0.5 Parts by weight |

C-1: compound 1 (produced in Example 1)

C-5: compound 5 (produced in Example 5)

P-1: 2,10-dimethyl-4,8-di-t-butyl-6-{2-[3-(3-t-butyl-4-hydroxy-5-methylphenyl) propionyloxy]ethoxy}-12H-dibenzo[d,g][1,3,2]dioxaphosphosine The above formulating materials were kneaded (dry blend) and then, using a laboplasto mill, kneaded at 300° C., 80 rpm for 5 minutes. The torque value after 5 minutes is shown in Table 3. The higher the torque value after 5 minutes, the better the processing stability becomes, because nylon 6 is decomposed by deterioration to reduce the torque value.

TABLE 3

|  | Example | | Comparative Example | |
|---|---|---|---|---|
|  | 1 | 2 | 1 | 2 |
| Test compound | C-1 | C-2 | — | P-1 |
| Torque value (kgf) | 38 | 36 | 22 | 27 |

What is claimed is:

1. A phosphite represented by the formula (I):

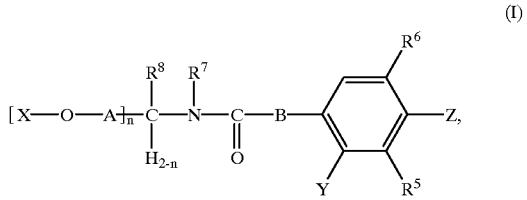

(I)

wherein n represents 1 or 2;

A represents an alkylene group having 1 to 8 carbon atoms;

B represents a direct bond or an alkylene group having 1 to 8 carbon atoms;

one of Y and Z represents a hydroxyl group, an alkoxy group having 1 to 8 carbon atoms or an aralkyloxy group having 7 to 12 carbon atoms, and the other one represents a hydrogen atom or an alkyl group having 1 to 8 carbon atoms;

X represents a phosphorous-containing group represented by the formula (II):

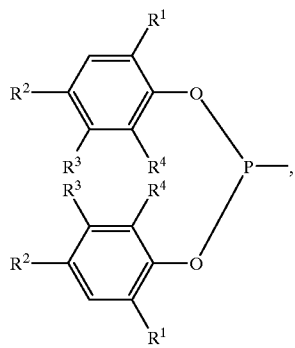

(II)

wherein $R^1$ and $R^2$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents a hydrogen atom or an alkyl group having 1 to 8 carbon atoms; and $R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ may be combined with each other to form a direct bond, a sulfur bond (—S—), or a methylene group which is optionally substituted with alkyl having 1 to 8 carbon atoms or cycloalkyl having 5 to 8 carbon atoms;

$R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group;

$R^8$ represents a hydrogen atom or an alkyl group having 1 to 8 carbon atoms; and $R^7$ represents a hydrogen atom or an alkyl group having 1 to 8 carbon atoms when n is 2, or $R^7$ represents a hydrogen atom, an alkyl group having 1 to 8 carbon atoms or a group of —CH($R^8$)—A—O—X (in which $R^8$, A and X are as defined above) when n is 1.

2. A process for producing the phosphite according to claim 1, which comprises reacting phenols or bisphenols represented by the following formula (III):

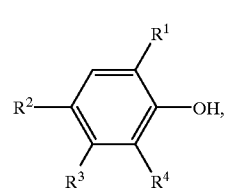

(III)

wherein $R^1$, $R^2$, $R^3$ and $R^4$ are as defined above, phosphorous trihalide and an alcohol represented by the formula (IV):

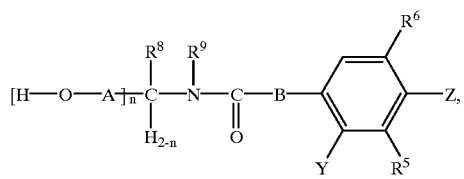

wherein n, A, B, Y, Z, $R^5$, $R^6$ and $R^8$ are as defined in claim 1; and $R^9$ represents a hydrogen atom or an alkyl group having 1 to 8 carbon atoms when n is 2, or $R^9$ represents a hydrogen atom, an alkyl group having 1 to 8 carbon atoms or a group of —CH($R^8$)—A—O—H (in which $R^8$ and A are as defined in claim 1) when n is 1.

3. A stabilizer for an organic material which comprises the phosphite according to claim 1.

4. A composition which comprises a phosphite according to claim 1 and an organic material selected from the group consisting of:

a polyethylene,
a polypropylene,
methylpentene polymer,
ethylene/ethyl acrylate copolymer resin,
ethylene/vinyl acetate copolymer resin,
polystyrene,
acrylonitrile/styrene copolymer resin,
acrylonitrile/butadiene/styrene copolymer resin,
an acrylic rubber/acrylonitrile/styrene copolymer resin,
an acrylonitrile/chlorinated polyethylene/styrene copolymer resin,
chlorinated polyethylene, polychloroprene, chlorinated rubber,
polyvinyl chloride, polyvinylidene chloride,
methacrylic resin,
ethylene/vinyl alcohol copolymer resin,
fluororesin,
polyacetal,
a grafted polyphenylene ether resin, polyphenylene sulfide resin,
polyurethane,
polyamide,
polyester resin,
polycarbonate,
polyacrylate,
polysulfone, polyether ether ketone, polyether sulfone,
epoxy resin,
diallyl phthalate prepolymer,
silicone resin,
unsaturated polyester resin,
acrylic-modified benzoguanamine resin,
benzoguanamine/melamine resin,
polybutadiene,
1,2-polybutadiene,
polyisoprene,
styrene/butadiene copolymer,
butadiene/acrylonitrile copolymer,
ethylene/propylene copolymer,
silicone rubber,
epichlorohydrin rubber,
acrylic rubber,
natural rubber,
chlorinated rubber paint,
polyester resin paint,
urethane resin paint,
epoxy resin paint,
acrylic resin paint,
vinyl resin paint,
aminoalkyd resin paint,
alkyd resin,
nitrocellulose resin paint,
oil-based paint,
wax, and
lubricating oil.

5. A composition which comprises a phosphite according to claim 1 and an organic material, wherein the organic material is a thermoplastic resin.

6. The composition according to claim 5, wherein the thermoplastic resin is a polyolefin or an engineering resin.

7. A composition according to claim 5, wherein thermoplastic resin comprises a polyester resin.

8. A composition according to claim 4, wherein said polyester resin is polyethylene terephthalate or polybutylene terephthalate.

9. A composition according to claim 5, wherein said thermoplastic resin comprises an aromatic polymer resin.

* * * * *